(12) United States Patent
Brondyk et al.

(10) Patent No.: US 7,317,095 B2
(45) Date of Patent: Jan. 8, 2008

(54) MUTANT GLYCOPROTEINS

(75) Inventors: William H. Brondyk, Mansfield, MA (US); Xuliang Jiang, Braintree, MA (US); Robert Campbell, Wrentham, MA (US)

(73) Assignee: Applied Research Systems ARS Holding N.V., Curacao (AN)

( * ) Notice: Subject to any disclaimer, the term of this patent is extended or adjusted under 35 U.S.C. 154(b) by 272 days.

(21) Appl. No.: 10/493,540

(22) PCT Filed: Oct. 22, 2002

(86) PCT No.: PCT/US02/33770

§ 371 (c)(1),
(2), (4) Date: Nov. 17, 2004

(87) PCT Pub. No.: WO2004/050679

PCT Pub. Date: Jun. 17, 2004

(65) Prior Publication Data

US 2005/0119465 A1   Jun. 2, 2005

Related U.S. Application Data

(60) Provisional application No. 60/337,590, filed on Oct. 22, 2001.

(51) Int. Cl.
*C07K 14/59* (2006.01)
*C12N 15/00* (2006.01)
*C12N 15/63* (2006.01)
*C12N 5/00* (2006.01)

(52) U.S. Cl. .................. 530/397; 424/198.1; 435/69.4; 435/320.1; 530/398; 536/23.2; 536/23.5; 536/23.51

(58) Field of Classification Search ............. 424/198.1; 435/69.4; 530/397; 536/23.51
See application file for complete search history.

(56) References Cited

U.S. PATENT DOCUMENTS 5,792,460 A * 8/1998 Boime .................. 424/192.1

FOREIGN PATENT DOCUMENTS

| WO | WO 88/10270 A1 | 12/1988 |
| WO | WO 96/07750 A1 | 3/1996 |
| WO | WO 01/58493 A1 | 8/2001 |

OTHER PUBLICATIONS

Bello et al., Cloning and DNA sequence analysis of the cDNA for the common alpha subunit of the ovine pituitary glycoprotein hormones, 1989, Nucleic acids Research, vol. 17, No. 24, pp. 10494.*

Rathnam et al., Isolation and amino acid sequence of the alpha subunit of follicle-stimulating hormone from equine pituitary glands, 1978, The Journal of Biological Chemistry, vol. 253, Issue 15, pp. 5355-5362.*

Bishop et al., Both the beta-subunit carbohydrate residues of follicle-stimulating hormone determine the metabolic clearance rate and in Vivo potency, 1995, vol. 136, No. 6, pp. 2635-2640.*

Bousfield et al., Structural features of mammalian gonadotropins, 1996, Molecular and Cellular Endocrinology, vol. 125, pp. 3-19.*

Wang et al., Rapid analysis of gene expression (RAGE) facilitates universal expression profiling, 1999, Nucleic acids Research, vol. 27, No. 23, pp. 4609-4618.*

Kaufman et al., Transgenic analysis of a 100-kb human beta-globin cluster-containing DNA fragment propagated as a bacterial artificial chromosome, 1999, vol. 94, No. 9, pp. 3178-3184.*

Baird, D., Is there a place for different isoforms of FSH in clinical medicine, 2001, Human Reproduction, vol. 16, Issue 7, pp. 1316-1318.*

Macklon et al., Follicule-Stimulating Hormone and advanced follicle development in the human, 2001, Archives of Medical Research, vol. 32, pp. 595-600.*

Palagiano et al., FSH: urinary and recombinant, 2004, European Journal of Obstetrics and Gynecology and Reproductive Biology, vol. 115S, pp. S30-S33.*

Fox, et al., "Three-Dimensional Structure of Human Follicle-Stimulating Hormone", Molecular Endocrinology. (2001), vol. 15, No. 3, 378-389.

Jiang, et al., "Structural Predictions for the Ligand-Binding Region of Glycoprotein Hormone Receptors and the Nature of Hormone-Receptor Interactions", Structure. (Dec. 15, 1995), vol. 3, No. 12, 1341-1353.

Lapthorn, et al., "Crystal Structure of Human Chorionic Gonadotropin", Nature. (Jun. 9, 1994), vol. 369, 455-461.

Tegoni, et al., "Crystal Structure of a Ternary Complex Between Human Chorionic Gonadotropin (hCG) and Two Fv Fragments Specific for the Alpha and Beta-Subunits", Journal of Molecular Biology.( Jun. 25, 1999), vol. 289, No. 5, 1375-1385, Abstract.

Wu, et al., "Structure of Human Chorionic Gonadotropin at 2.6 Å Resolution from MAD Analysis of the Selenomethionyl Protein", Structure. (Jun. 15, 1994), vol. 2, No. 6, 545-558.

* cited by examiner

*Primary Examiner*—Manjunath N. Rao
*Assistant Examiner*—Ian Dang
(74) *Attorney, Agent, or Firm*—Browdy & Neimark, PLLC

(57) ABSTRACT

The inventors have designed novel FSH mutants with increased glycosylation and longer half-lives for use in inducing folliculogenesis in human patients. The use of a FSH mutant preparation of the invention permits the use of lower cumulative doses of FSH to achieve the same or better clinical result.

23 Claims, 7 Drawing Sheets

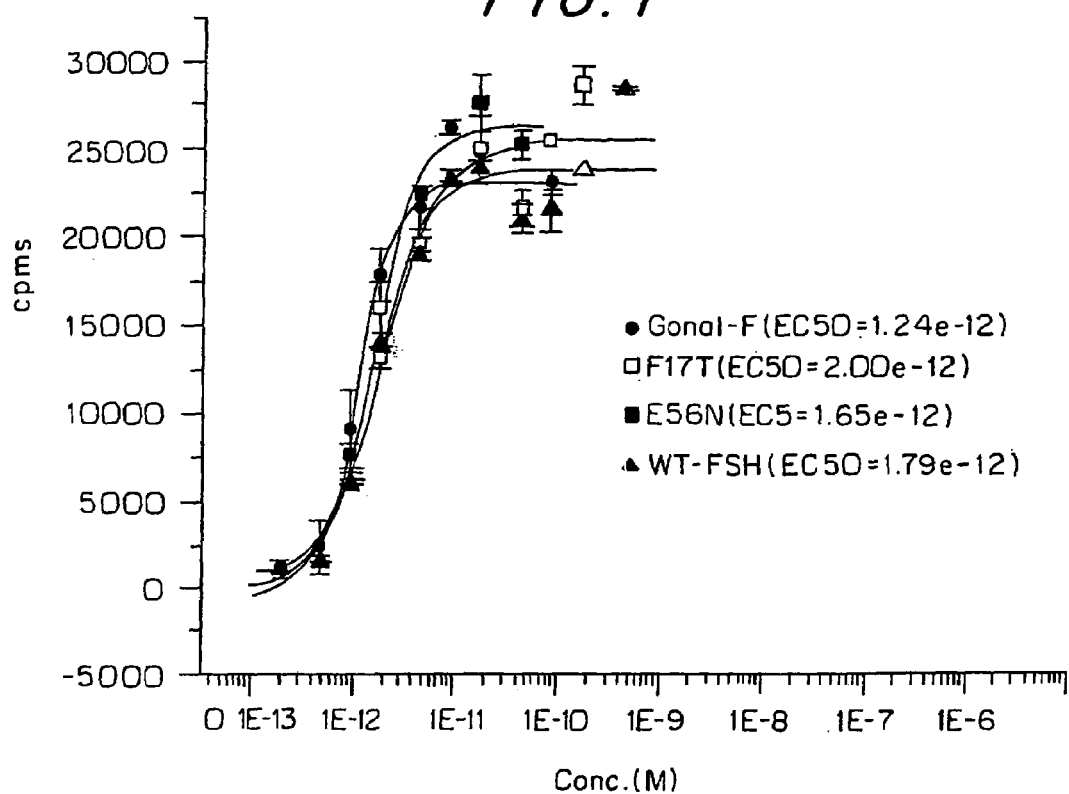
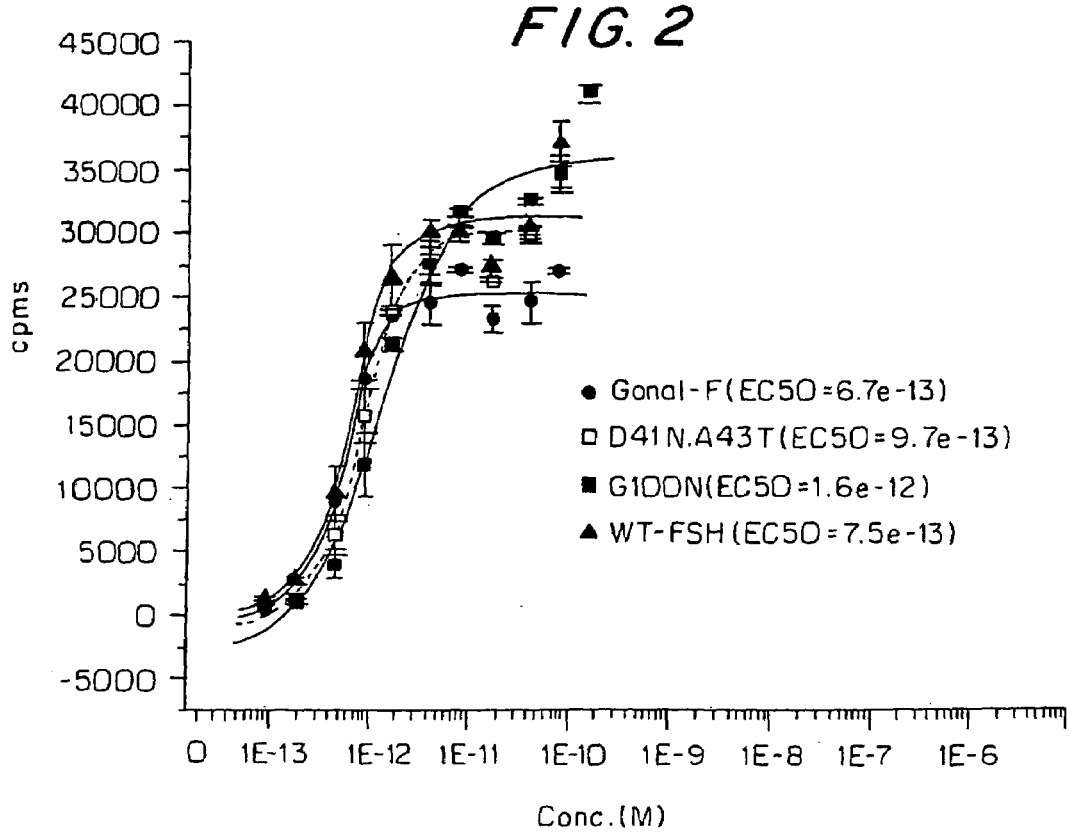

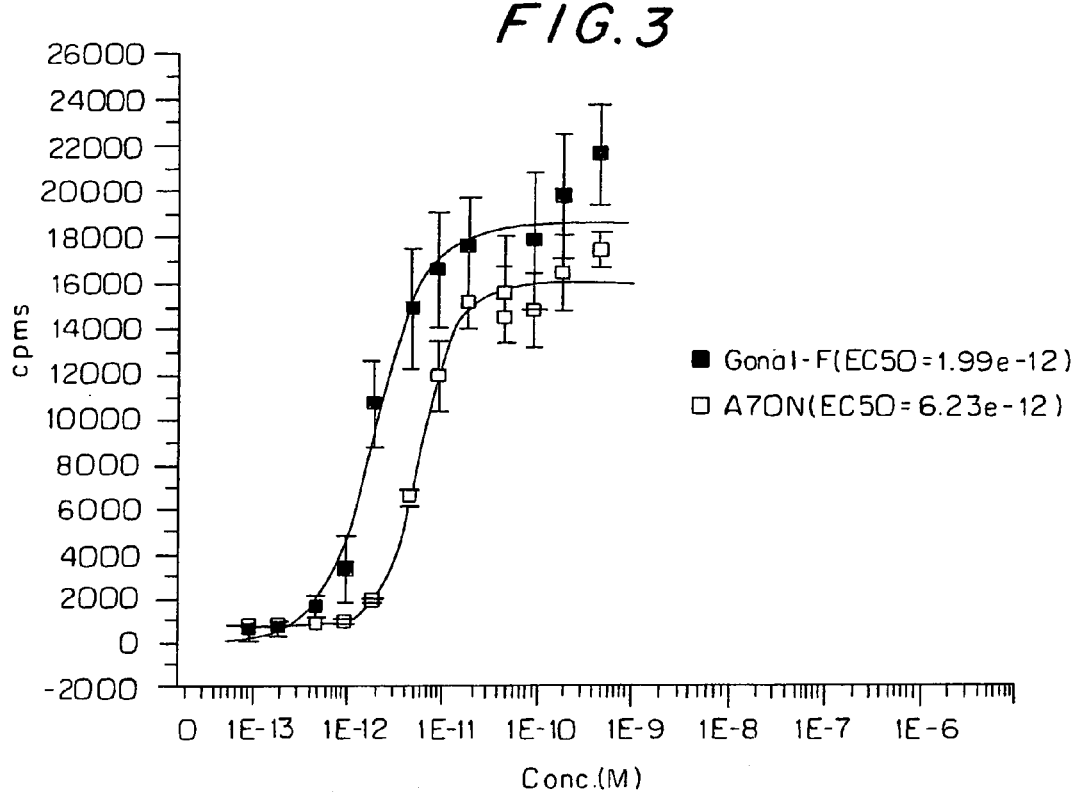
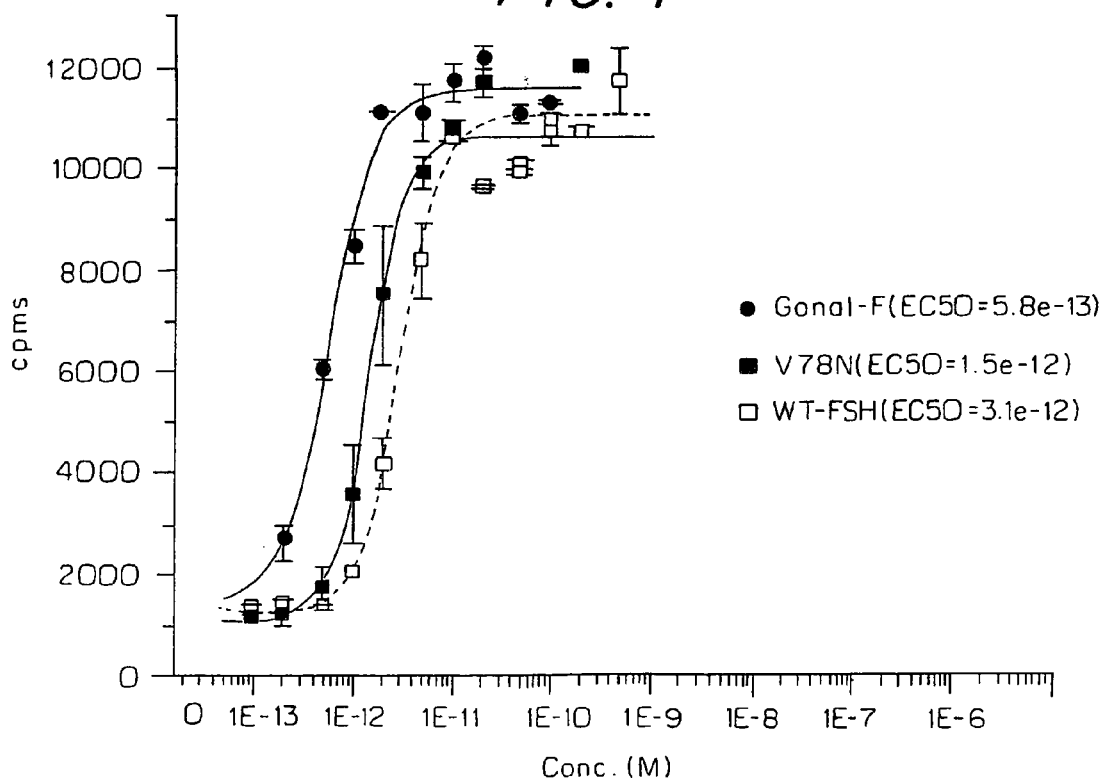

FIG. 6

Ala Pro Asp Val Gln Asp Cys Pro Glu Cys Thr Leu Gln Glu Asn Pro
1           5                   10                  15
Phe Phe Ser Gln Pro Gly Ala Pro Ile Leu Gln Cys Met Gly Cys Cys
            20                  25                  30
Phe Ser Arg Ala Tyr Pro Thr Pro Leu Arg Ser Lys Lys Thr Met Leu
            35                  40                  45
Val Gln Lys Asn Val Thr Ser Glu Ser Thr Cys Cys Val Ala Lys Ser
      50                  55                  60
Tyr Asn Arg Val Thr Val Met Gly Gly Phe Lys Val Glu Asn His Thr
65                  70                  75
Ala Cys His Cys Ser Thr Cys Tyr Tyr His Lys Ser
            85                  90

FIG. 7

Asn Ser Cys Glu Leu Thr Asn Ile Thr Ile Ala Ile Glu Lys Glu Glu
1           5                   10                  15
Cys Arg Phe Cys Ile Ser Ile Asn Thr Thr Trp Cys Ala Gly Tyr Cys
            20                  25                  30
Tyr Thr Arg Asp Leu Val Tyr Lys Asp Pro Ala Arg Pro Lys Ile Gln
            35                  40                  45
Lys Thr Cys Thr Phe Lys Glu Leu Val Tyr Glu Thr Val Arg Val Pro
        50                  55                  60
Gly Cys Ala His His Ala Asp Ser Leu Tyr Thr Tyr Pro Val Ala Thr
65                  70                  75                  80
Gln Cys His Cys Gly Lys Cys Asp Ser Asp Ser Thr Asp Cys Thr Val
            85                  90
Arg Gly Leu Gly Pro Ser Tyr Cys Ser Phe Gly Glu Met Lys Glu
        100                 105                 110

FIG. 8

Ala Pro Asp Val Gln Asp Cys Pro Glu Cys Thr Leu Gln Glu Asn Pro
1          5                    10                   15
Thr Phe Ser Gln Pro Gly Ala Pro Ile Leu Gln Cys Met Gly Cys Cys
        20                  25                  30
Phe Ser Arg Ala Tyr Pro Thr Pro Leu Arg Ser Lys Lys Thr Met Leu
    35                  40                  45
Val Gln Lys Asn Val Thr Ser Glu Ser Thr Cys Cys Val Ala Lys Ser
    50                  55                  60
Tyr Asn Arg Val Thr Val Met Gly Gly Phe Lys Val Glu Asn His Thr
65                  70                  75                  80
Ala Cys His Cys Ser Thr Cys Tyr Tyr His Lys Ser
            85                  90

FIG. 9

Ala Pro Asp Val Gln Asp Cys Pro Glu Cys Thr Leu Gln Glu Asn Pro
1          5                    10                   15
Phe Phe Ser Gln Pro Gly Ala Pro Ile Leu Gln Cys Met Gly Cys Cys
        20                  25                  30
Phe Ser Arg Ala Tyr Pro Thr Pro Leu Arg Ser Lys Lys Thr Met Leu
    35                  40                  45
Val Gln Lys Asn Val Thr Ser Asn Ser Thr Cys Cys Val Ala Lys Ser
    50                  55                  60
Tyr Asn Arg Val Thr Val Met Gly Gly Phe Lys Val Glu Asn His Thr
65                  70                  75                  80
Ala Cys His Cys Ser Thr Cys Tyr Tyr His Lys Ser
            85                  90

FIG. 10

Asn Ser Cys Glu Leu Thr Asn Ile Thr Ile Ala Ile Glu Lys Glu Glu
1          5                    10                   15
Cys Arg Phe Cys Ile Ser Ile Asn Thr Thr Trp Cys Ala Gly Tyr Cys
            20                  25                  30
Tyr Thr Arg Asp Leu Val Tyr Lys Asp Pro Ala Arg Pro Lys Ile Gln
            35                  40                  45
Lys Thr Cys Thr Phe Lys Glu Leu Val Tyr Glu Thr Val Arg Val Pro
      50              55                  60
Gly Cys Ala His His Asn Asp Ser Leu Tyr Thr Tyr Pro Val Ala Thr
65                  70                  75                  80
Gln Cys His Cys Gly Lys Cys Asp Ser Asp Ser Thr Asp Cys Thr Val
            85                  90                  95
Arg Gly Leu Gly Pro Ser Tyr Cys Ser Phe Gly Glu Met Lys Glu
            100                 105                 110

FIG. 11

Asn Ser Cys Glu Leu Thr Asn Ile Thr Ile Ala Ile Glu Lys Glu Glu
1          5                    10                  15
Cys Arg Phe Cys Ile Ser Ile Asn Thr Thr Trp Cys Ala Gly Tyr Cys
            20                  25                  30
Tyr Thr Arg Asp Leu Val Tyr Lys Asp Pro Ala Arg Pro Lys Ile Gln
            35                  40                  45
Lys Thr Cys Thr Phe Lys Glu Leu Val Tyr Glu Thr Val Arg Val Pro
      50              55                  60
Gly Cys Ala His His Ala Asp Ser Leu Tyr Thr Tyr Pro Asn Ala Thr
65                  70                  75                  80
Gln Cys His Cys Gly Lys Cys Asp Ser Asp Ser Thr Asp Cys Thr Val
            85                  90                  95
Arg Gly Leu Gly Pro Ser Tyr Cys Ser Phe Gly Glu Met Lys Glu
            100                 105                 110

FIG. 12

Asn Ser Cys Glu Leu Thr Asn Ile Thr Ile Ala Ile Glu Lys Glu Glu
1             5                    10                   15
Cys Arg Phe Cys Ile Ser Ile Asn Thr Thr Trp Cys Ala Gly Tyr Cys
              20                   25                   30
Tyr Thr Arg Asp Leu Val Tyr Lys  Asp Pro Ala Arg Pro Lys Ile Gln
              35                   40                   45
Lys Thr Cys Thr Phe Lys Glu Leu Val Tyr Glu Thr Val Arg Val Pro
      50                   55                   60
Gly Cys Ala His His Ala Asp Ser Leu Tyr Thr Tyr Pro Val Ala Thr
65                   70                   75                   80
Gln Cys His Cys Gly Lys Cys Asp Ser Asp Ser Thr Asp Cys Thr Val
              85                   90                   95
Arg Gly Leu Asn Pro Ser Tyr Cys Ser Phe Gly Glu Met Lys Glu
              100                  105                  110

FIG. 13

Asn Ser Cys Glu Leu Thr Asn Ile Thr Ile Ala Ile Glu Lys Glu Glu
1             5                    10                   15
Cys Arg Phe Cys Ile Ser Ile Asn Thr Thr Trp Cys Ala Gly Tyr Cys
              20                   25                   30
Tyr Thr Arg Asp Leu Val Tyr Lys  Asn Pro Thr Arg Pro Lys Ile Gln
              35                   40                   45
Lys Thr Cys Thr Phe Lys Glu Leu Val Tyr Glu Thr Val Arg Val Pro
      50                   55                   60
Gly Cys Ala His His Ala Asp Ser Leu Tyr Thr Tyr Pro Val Ala Thr
65                   70                   75                   80
Gln Cys His Cys Gly Lys Cys Asp Ser Asp Ser Thr Asp Cys Thr Val
              85                   90                   95
Arg Gly Leu Gly Pro Ser Tyr Cys Ser Phe Gly Glu Met Lys Glu
              100                  105                  110

SEQUENCE LISTING

```
<160> NUMBER OF SEQ ID NOS: 20

<210> SEQ ID NO 1
<211> LENGTH: 92
<212> TYPE: PRT
<213> ORGANISM: Homo sapiens

<400> SEQUENCE: 1

Ala Pro Asp Val Gln Asp Cys Pro Glu Cys Thr Leu Gln Glu Asn Pro
1               5                   10                  15

Phe Phe Ser Gln Pro Gly Ala Pro Ile Leu Gln Cys Met Gly Cys Cys
            20                  25                  30

Phe Ser Arg Ala Tyr Pro Thr Pro Leu Arg Ser Lys Lys Thr Met Leu
        35                  40                  45

Val Gln Lys Asn Val Thr Ser Glu Ser Thr Cys Cys Val Ala Lys Ser
    50                  55                  60

Tyr Asn Arg Val Thr Val Met Gly Gly Phe Lys Val Glu Asn His Thr
65                  70                  75                  80

Ala Cys His Cys Ser Thr Cys Tyr Tyr His Lys Ser
                85                  90

<210> SEQ ID NO 2
<211> LENGTH: 111
<212> TYPE: PRT
<213> ORGANISM: Homo sapiens

<400> SEQUENCE: 2

Asn Ser Cys Glu Leu Thr Asn Ile Thr Ile Ala Ile Glu Lys Glu Glu
1               5                   10                  15

Cys Arg Phe Cys Ile Ser Ile Asn Thr Thr Trp Cys Ala Gly Tyr Cys
            20                  25                  30

Tyr Thr Arg Asp Leu Val Tyr Lys Asp Pro Ala Arg Pro Lys Ile Gln
        35                  40                  45

Lys Thr Cys Thr Phe Lys Glu Leu Val Tyr Glu Thr Val Arg Val Pro
    50                  55                  60

Gly Cys Ala His His Ala Asp Ser Leu Tyr Thr Tyr Pro Val Ala Thr
65                  70                  75                  80
```

```
Gln Cys His Cys Gly Lys Cys Asp Ser Asp Ser Thr Asp Cys Thr Val
                85                  90                  95

Arg Gly Leu Gly Pro Ser Tyr Cys Ser Phe Gly Glu Met Lys Glu
            100                 105                 110

<210> SEQ ID NO 3
<211> LENGTH: 92
<212> TYPE: PRT
<213> ORGANISM: Homo sapiens

<400> SEQUENCE: 3

Ala Pro Asp Val Gln Asp Cys Pro Glu Cys Thr Leu Gln Glu Asn Pro
1               5                   10                  15

Thr Phe Ser Gln Pro Gly Ala Pro Ile Leu Gln Cys Met Gly Cys Cys
            20                  25                  30

Phe Ser Arg Ala Tyr Pro Thr Pro Leu Arg Ser Lys Lys Thr Met Leu
        35                  40                  45

Val Gln Lys Asn Val Thr Ser Glu Ser Thr Cys Cys Val Ala Lys Ser
50                  55                  60

Tyr Asn Arg Val Thr Val Met Gly Gly Phe Lys Val Glu Asn His Thr
65                  70                  75                  80

Ala Cys His Cys Ser Thr Cys Tyr Tyr His Lys Ser
                85                  90

<210> SEQ ID NO 4
<211> LENGTH: 92
<212> TYPE: PRT
<213> ORGANISM: Homo sapiens

<400> SEQUENCE: 4

Ala Pro Asp Val Gln Asp Cys Pro Glu Cys Thr Leu Gln Glu Asn Pro
1               5                   10                  15

Phe Phe Ser Gln Pro Gly Ala Pro Ile Leu Gln Cys Met Gly Cys Cys
            20                  25                  30

Phe Ser Arg Ala Tyr Pro Thr Pro Leu Arg Ser Lys Lys Thr Met Leu
        35                  40                  45

Val Gln Lys Asn Val Thr Ser Asn Ser Thr Cys Cys Val Ala Lys Ser
50                  55                  60

Tyr Asn Arg Val Thr Val Met Gly Gly Phe Lys Val Glu Asn His Thr
65                  70                  75                  80

Ala Cys His Cys Ser Thr Cys Tyr Tyr His Lys Ser
                85                  90

<210> SEQ ID NO 5
<211> LENGTH: 111
<212> TYPE: PRT
<213> ORGANISM: Homo sapiens

<400> SEQUENCE: 5

Asn Ser Cys Glu Leu Thr Asn Ile Thr Ile Ala Ile Glu Lys Glu Glu
1               5                   10                  15

Cys Arg Phe Cys Ile Ser Ile Asn Thr Thr Trp Cys Ala Gly Tyr Cys
            20                  25                  30

Tyr Thr Arg Asp Leu Val Tyr Lys Asp Pro Ala Arg Pro Lys Ile Gln
        35                  40                  45

Lys Thr Cys Thr Phe Lys Glu Leu Val Tyr Glu Thr Val Arg Val Pro
50                  55                  60
```

```
Gly Cys Ala His His Asn Asp Ser Leu Tyr Thr Tyr Pro Val Ala Thr
 65                  70                  75                  80

Gln Cys His Cys Gly Lys Cys Asp Ser Asp Ser Thr Asp Cys Thr Val
                 85                  90                  95

Arg Gly Leu Gly Pro Ser Tyr Cys Ser Phe Gly Glu Met Lys Glu
                100                 105                 110

<210> SEQ ID NO 6
<211> LENGTH: 111
<212> TYPE: PRT
<213> ORGANISM: Homo sapiens

<400> SEQUENCE: 6

Asn Ser Cys Glu Leu Thr Asn Ile Thr Ile Ala Ile Glu Lys Glu Glu
 1               5                  10                  15

Cys Arg Phe Cys Ile Ser Ile Asn Thr Thr Trp Cys Ala Gly Tyr Cys
                20                  25                  30

Tyr Thr Arg Asp Leu Val Tyr Lys Asp Pro Ala Arg Pro Lys Ile Gln
                35                  40                  45

Lys Thr Cys Thr Phe Lys Glu Leu Val Tyr Glu Thr Val Arg Val Pro
 50                  55                  60

Gly Cys Ala His His Ala Asp Ser Leu Tyr Thr Tyr Pro Asn Ala Thr
 65                  70                  75                  80

Gln Cys His Cys Gly Lys Cys Asp Ser Asp Ser Thr Asp Cys Thr Val
                 85                  90                  95

Arg Gly Leu Gly Pro Ser Tyr Cys Ser Phe Gly Glu Met Lys Glu
                100                 105                 110

<210> SEQ ID NO 7
<211> LENGTH: 111
<212> TYPE: PRT
<213> ORGANISM: Homo sapiens

<400> SEQUENCE: 7

Asn Ser Cys Glu Leu Thr Asn Ile Thr Ile Ala Ile Glu Lys Glu Glu
 1               5                  10                  15

Cys Arg Phe Cys Ile Ser Ile Asn Thr Thr Trp Cys Ala Gly Tyr Cys
                20                  25                  30

Tyr Thr Arg Asp Leu Val Tyr Lys Asp Pro Ala Arg Pro Lys Ile Gln
                35                  40                  45

Lys Thr Cys Thr Phe Lys Glu Leu Val Tyr Glu Thr Val Arg Val Pro
 50                  55                  60

Gly Cys Ala His His Ala Asp Ser Leu Tyr Thr Tyr Pro Val Ala Thr
 65                  70                  75                  80

Gln Cys His Cys Gly Lys Cys Asp Ser Asp Ser Thr Asp Cys Thr Val
                 85                  90                  95

Arg Gly Leu Asn Pro Ser Tyr Cys Ser Phe Gly Glu Met Lys Glu
                100                 105                 110

<210> SEQ ID NO 8
<211> LENGTH: 111
<212> TYPE: PRT
<213> ORGANISM: Homo sapiens

<400> SEQUENCE: 8

Asn Ser Cys Glu Leu Thr Asn Ile Thr Ile Ala Ile Glu Lys Glu Glu
 1               5                  10                  15

Cys Arg Phe Cys Ile Ser Ile Asn Thr Thr Trp Cys Ala Gly Tyr Cys
```

|  | 20 | 25 | 30 |

Tyr Thr Arg Asp Leu Val Tyr Lys Asn Pro Thr Arg Pro Lys Ile Gln
            35                  40                  45

Lys Thr Cys Thr Phe Lys Glu Leu Val Tyr Glu Thr Val Arg Val Pro
 50                  55                  60

Gly Cys Ala His His Ala Asp Ser Leu Tyr Thr Tyr Pro Val Ala Thr
 65                  70                  75                  80

Gln Cys His Cys Gly Lys Cys Asp Ser Asp Ser Thr Asp Cys Thr Val
                    85                  90                  95

Arg Gly Leu Gly Pro Ser Tyr Cys Ser Phe Gly Glu Met Lys Glu
                    100                 105                 110

<210> SEQ ID NO 9
<211> LENGTH: 35
<212> TYPE: DNA
<213> ORGANISM: Artificial
<220> FEATURE:
<223> OTHER INFORMATION: Synthetic

<400> SEQUENCE: 9
ccttgtatac atacccaaac gccacccagt gtcac                          35

<210> SEQ ID NO 10
<211> LENGTH: 35
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: V78N

<400> SEQUENCE: 10
gtgacactgg gtggcgtttg ggtatgtata caagg                          35

<210> SEQ ID NO 11
<211> LENGTH: 36
<212> TYPE: DNA
<213> ORGANISM: Artificial
<220> FEATURE:
<223> OTHER INFORMATION: Synthetic

<400> SEQUENCE: 11
gctgtgctca ccataacgat tccttgtata catacc                         36

<210> SEQ ID NO 12
<211> LENGTH: 36
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: A70N

<400> SEQUENCE: 12
ggtatgtata caaggaatcg ttatggtgag cacagc                         36

<210> SEQ ID NO 13
<211> LENGTH: 38
<212> TYPE: DNA
<213> ORGANISM: Artificial
<220> FEATURE:
<223> OTHER INFORMATION: Synthetic

```
<400> SEQUENCE: 13
gatctggtgt ataagaaccc aactaggccc aaaatcca                              38

<210> SEQ ID NO 14
<211> LENGTH: 38
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: D41N/A43T

<400> SEQUENCE: 14
tggattttgg gcctagttgg gttcttatac accagatc                              38

<210> SEQ ID NO 15
<211> LENGTH: 36
<212> TYPE: DNA
<213> ORGANISM: Artificial
<220> FEATURE:
<223> OTHER INFORMATION: Synthetic

<400> SEQUENCE: 15
tgtactgtgc gaggcctgaa ccccagctac tgctcc                                36

<210> SEQ ID NO 16
<211> LENGTH: 36
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: G100N

<400> SEQUENCE: 16
ggagcagtag ctggggttca ggcctcgcac agtaca                                36

<210> SEQ ID NO 17
<211> LENGTH: 27
<212> TYPE: DNA
<213> ORGANISM: Artificial
<220> FEATURE:
<223> OTHER INFORMATION: Synthetic

<400> SEQUENCE: 17
gaacgtcacc tcaaactcca cttgctg                                          27

<210> SEQ ID NO 18
<211> LENGTH: 27
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: E56N

<400> SEQUENCE: 18
cagcaagtgg agtttgaggt gacgttc                                          27

<210> SEQ ID NO 19
<211> LENGTH: 26
<212> TYPE: DNA
<213> ORGANISM: Artificial
<220> FEATURE:
```

```
<223> OTHER INFORMATION: Synthetic

<400> SEQUENCE: 19
caggaaaacc caaccttctc ccagcc                                              26

<210> SEQ ID NO 20
<211> LENGTH: 26
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: F17T

<400> SEQUENCE: 20
ggctgggaga aggttgggtt ttcctg                                              26
```

MUTANT GLYCOPROTEINS

FIELD OF INVENTION

The invention relates to the field of gonadotrophins, and particularly their use in the treatment of reproductive disorders.

BACKGROUND OF THE INVENTION

The gonadotrophins are a group of heterodimeric glycoproteins including follicle stimulating hormone (FSH), luteinising hormone (LH) and chorionic gonadotrophin (CG). These hormones regulate gonadal function in the male and female. Each of these hormones is composed of two non-covalently linked subunits: an alpha-subunit, which is common to FSH, LH and hCG, and a beta-subunit, which is unique to each of them, and which confers biological specificity to each hormone.

In all of the gonadotrophins, each sub-unit has asparagine-linked (N-linked) oligosaccharides side chains. In the common alpha-subunit of the human hormones, these are attached at positions 52 and 78. In both human FSH and CG, two N-linked oligosaccharide side chains are attached to the beta-subunit, at positions 7 and 24 in FSH, and positions 13 and 30 in hCG. In human LH, one oligosaccharide is attached at position 30 of the beta-subunit. hCG has additionally four serine-linked (O-linked) oligosaccharide side chains, present in the carboxyl terminal portion (CTP).

The gonadotrophins play crucial roles in the reproductive cycle, and their use is essential for assisted reproductive techniques (ART), such as in vitro fertilisation (IVF), IVF in conjunction with intracytoplasmic sperm injection (IVF/ICSI) and embryo transfer (ET), as well as for ovulation induction (OI) in anovulatory patients undergoing in vivo fertilisation either naturally or through intrauterine insemination (IUI).

ART is typically carried out using controlled ovarian hyperstimulation (COH) to increase the number of female gametes. Standard regimens for COH include a down-regulation phase in which endogenous gonadotrophins are suppressed by administration of a gonadotrophin releasing hormone (GnRH) agonist followed by a stimulatory phase in which follicular development (folliculogenesis) is induced by daily administration of FSH, usually at about 150-225 IU/day. Alternatively stimulation is started after spontaneous or induced menstruation while preventing the occurrence of an ill-timed LH surge by administration of a GnRH-antagonist (typically starting around day six of the stimulatory phase). When there are at least 3 follicles>16 mm (one of 18 mm), a single bolus of hCG (5-10,000 IU) is given to mimic the natural LH surge and induce ovulation. Oocyte recovery is timed for 36-38 hours after the hCG injection.

OI is typically carried out with daily administration of FSH at a dose of about 75-150 IU/day. Down-regulation with GnRH agonists or antagonists may be used, although less frequently than in the ART indication. hCG is given to mimic the LH surge prior to in vivo fertilisation which is achieved either through regular intercourse or IUI.

The typical regimens described above for ART and OI require daily injections of gonadotrophins over a prolonged period, i.e. for an average of 10 days, and up to 21 days in some patients. The development of FSH preparations of increased efficacy would permit the daily dosage of FSH to be decreased, and/or permit a shortening of the treatment period (i.e. fewer injections), and/or allow injections to be given less frequently. This would render ART and OI regimens more convenient and patient-friendly.

Furthermore, ART using in vitro fertilisation is fraught with possible mishaps. For example, not every follicle will produce a viable oocyte, not every viable oocyte will be successfully fertilised, and some embryos may not be viable. Moreover, once viable embryos are selected, transfer to the uterus and implantation may not be successful. In order to maximise the chances of a live birth it is therefore desirable to stimulate the growth and maturation of several follicles, to ensure the collection of multiple oocytes.

In the indication of OI, in contrast, the objective is to obtain not more than three and preferably one dominant follicle (to avoid multiple pregnancies).

Some patients undergoing ART and OI present a reduced number of growing follicles when treated with conventional FSH preparations. This is a limiting factor for success when undergoing ART, in that it limits the number of embryos available for transfer and/or cryopreservation. It can also be a limiting factor for success in patients undergoing IUI, where obtaining more than one follicle is important. Patients presenting this type of response include patients above about 33-35 years old, patients with elevated base-line FSH, elevated base-line oestradiol or reduced base-line inhibin b.

In the male, spermatogenesis is dependent on stimulation of Sertoli cells by FSH. FSH deficiency results in oligospermia, and hence infertility. The treatment of male infertility with conventional FSH preparations requires FSH injections three times a week for up to 18 months.

Modified FSH molecules, bearing additional glycosylation sites are described, in WO 01/58493 (Maxygen). One example of a modified FSH molecules is tested and reported to have a reduced bioactivity and an increased in vivo half-life.

The development of FSH preparations with enhanced ability to stimulate folliculogenesis, is an ongoing need. There is also an existing need for new FSH preparations to treat patients with a diminished response to FSH. Also desirable are FSH preparations of longer half-life, permitting shorter treatment protocols and/or decreased cumulative doses and/or less frequent dosing, for ART, OI and male infertility.

SUMMARY OF THE INVENTION

The inventors have designed novel FSH mutants with increased glycosylation and longer half-lives for use in treating reproductive disorders in human patients. The use of a FSH mutant preparation of the invention permits the use of lower cumulative doses of FSH to achieve the same or better clinical result.

Accordingly, the invention provides a mutant FSH showing FSH activity, the mutant FSH having at least one additional glycosylation site, as compared with wild type FSH, which glycosylation site bears a glycan. The invention further provides nucleic acid molecules encoding the mutant FSH. Also included in the invention is a vector containing any one of the nucleic acids of the present invention.

The present invention is also directed to recombinant host cells expressing a mutant FSH of the invention, particularly a host cell transformed with a vector comprising a FSH nucleic acid molecule encoding the mutant FSH. In further aspect, the invention provides for a composition that includes a mutant FSH and a pharmaceutically acceptable carrier or excipient.

Still further, the invention provides a method for producing a mutant FSH. The method includes providing a cell containing a FSH mutant nucleic acid, e.g., a vector that includes a FSH mutant nucleic acid, and culturing the cell under conditions sufficient to express the FSH mutant. The expressed FSH mutant is then recovered from the cell.

The present invention also provides for methods of treating male and female infertility, as well as reproductive disorders in mammals, including stimulating folliculogenesis, inducing ovulation and ovarian hyperstimulation.

In another aspect, the invention provides a use of mutant FSH in ovulation induction, stimulation of folliculogenesis and controlled ovarian hyperstimulation, particularly in conjuction with ART.

BRIEF DESCRIPTION OF THE FIGURES

FIG. 1 illustrates the dose-response FSH activity for mutants F17T and E56N, as compared to conventional recombinant FSH and wild type FSH.

FIG. 2 illustrates the dose-response FSH activity for mutants D41N/A43T and G100N, as compared to conventional recombinant FSH and wild type FSH.

FIG. 3 illustrates the dose-response FSH activity for mutant A70N, as compared to conventional recombinant FSH.

FIG. 4 illustrates the dose-response FSH activity for mutants F17T and E56, as compared to conventional recombinant FSH and wild type FSH.

FIG. 6 is the amino acid sequence for the mature human FSH alpha subunit (SEQ ID NO: 1).

FIG. 7 is the amino acid sequence for the mature human FSH beta subunit (SEQ ID NO: 2).

FIG. 8 is the amino acid sequence for FSH mutant F17T (SEQ ID NO: 3).

FIG. 9 is the amino acid sequence for FSH mutant E56N (SEQ ID NO: 4).

FIG. 10 is the amino acid sequence for FSH mutant A70N (SEQ ID NO: 5).

FIG. 11 is the amino acid sequence for FSH mutant V78N (SEQ ID NO: 6).

FIG. 12 is the amino acid sequence for FSH mutant G100N (SEQ ID NO: 7).

FIG. 13 is the amino acid sequence for FSH mutant D41N/A43T (SEQ ID NO: 8).

DETAILED DESCRIPTION OF THE INVENTION

Figure 5:
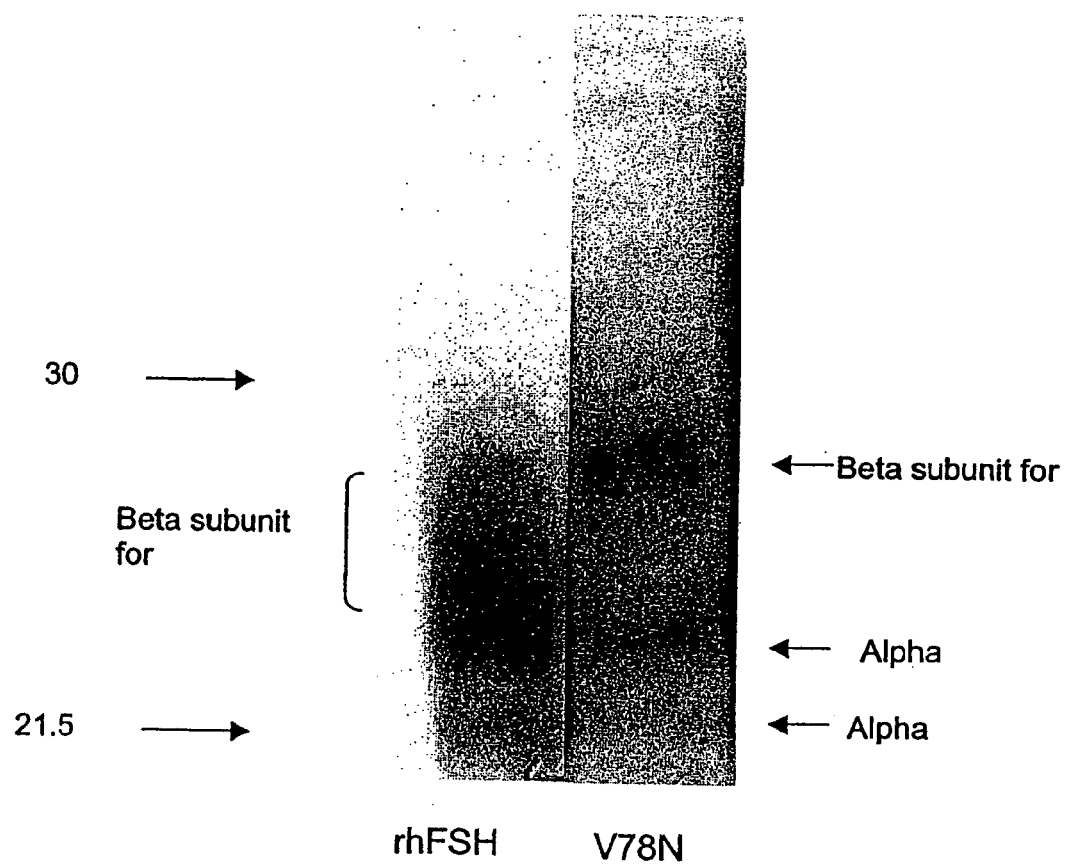
FIG. 5 is a representation of an electrophoretic gel demonstrating the higher molecular weight of mutant V78N, as compared with wild type FSH.

Based on information derived from the crystal structure of FSH, the inventors have designed mutants with increased glycosylation by substituting specific amino acids for asparagine or threonine, thereby creating additional glycosylation recognition sites.

The specific substitutions were as follows:
In the beta-subunit: A70N, V78N, G100N and D41N/A43T;
In the alpha-subunit: F17T and E56N.

It is known that potential in vivo N-glycosylation sites are specific to the consensus pattern Asn-Xaa-Ser/Thr, and less specifically to the pattern Asn-Xaa-Cys, where Xaa can be any amino acid residue. The probability of N-glycosylation for the Asn-Pro-Ser/Thr sequence is about 50%, which is statistically much lower than the other consensus pattern of Asn-Xaa-Ser/Thr. The presence of the consensus tripeptide, however, is not sufficient to conclude that an asparagine residue will be glycosylated.

Protein folding plays an important role in the regulation of N-glycosylation. If consensus residues are buried in the interior of the folded protein structure, it is unlikely glycosylation will occur at the particular site. Furthermore, if a glycosylation site is introduced by mutation, the mutated residues should not disrupt the three-dimensional structure of the protein or substantially detract from the desired function of the protein, such as receptor binding or activation. For these reasons, structural knowledge of the protein molecule is critical to the success of the design of glycosylation mutants.

Two methods that have been used to gain insight into the 3-dimensional structure of proteins are modeling and X-ray crystal structure. Although hCG and FSH have essentially identical folding patterns, the two structures are significantly different (Fox et al, 2001), and the detailed structure for individual amino acid residues for the FSH molecule cannot be properly modeled from the previously determined hCG structures (Wu et al, 1994; Lapthorn et al, 1994). The inventors have designed mutants based solely on the crystal structures of the human FSH molecule (Fox, et al, 2001).

There are two FSH molecules (four subunits) in each asymmetric unit in the crystal structure. These two molecules were superimposed and compared, and each residue was visually inspected to identify potential N-glycosylation sites that would not disrupt the structure of the protein molecule.

Structural knowledge was also analysed to uncover potential functional important regions of the glycoprotein hormone molecules, including FSH, hCG and TSH. Comparative study of the crystal structures of hCG molecule alone (Wu et al, 1994; Lapthorn et al, 1994) and its complex with the Fv fragments of neutralizing and non-neutralizing antibodies (Tegoni, et al, 1999) provided clues of the important regions for receptor binding and activation. One face of the "waist-like" region of the hCG molecule is very likely to bind to the extracellular domain of the receptor, and this type of interaction was inferred for the FSH-FSHR system.

Using structural knowledge, the FSH ligand (Fox et al, 2001) was fine tuned to its receptor model (Jiang et al, 1995). The following six site mutations were selected, all of which avoid the ligand-receptor interface on one side of the "waist-region" of the FSH molecule:

In the beta-subunit: A70N, V78N, G100N and D41N/A43T;
In the alpha-subunit: F17T and E56N;

wherein A is alanine, D is aspartic acid, E is glutamic acid, F is phenylalanine, G is glycine, N is asparagine, T is threonine, V is valine, and the notation "E4N" represents a replacement of a glutamic acid (E) at position 4 with an asparagine (N). For sequence numbering, the amino acid sequence of human FSH alpha is numbered according to the mature sequence shown in FIG. 6 or SEQ ID NO: 1. The amino acid sequence of human FSH beta is numbered according to the mature sequence shown in FIG. 7 or SEQ ID NO: 2.

Thus, the present invention relates to FSH preparations having increased half-life resulting from an increased glycosylation by adding one or more additional glycosylation sites on the protein. Such sites were introduced by substitution of residues in the FSH protein backbone with serine, threonine, lysine or asparagine residues, using, for example, mutagenesis. For in vivo glycosylation, the site introduced should be such as to form an "N-glycosylation site", of the following sequence: N-X'-S/T/C-X", wherein X' is any amino acid residue except proline, X" is any amino acid residue which may or may not be identical to X' and which preferably is different from proline, N is asparagine, and S/T/C represents a residue that may be serine, threonine or cysteine, preferably serine or threonine, and most preferably threonine.

Methods for Generating FSH Mutants:

The FSH mutants of the present invention may be produced by any suitable method known in the art. These methods include the construction of nucleotide sequences encoding the respective FSH mutants and expressing the amino acid sequence in a suitable transfected host. FSH mutants of the present invention may also be produced by chemical synthesis or by a combination of chemical synthesis and recombinant DNA technology.

FSH mutants of the present invention may comprise the FSH alpha and FSH beta subunits in the form of two separate polypeptide chains, where the two chains become dimerized in vivo so as to form a dimeric polypeptide, or it may comprise a single chain construct comprising the two subunits covalently linked by a peptide bond or a peptide linker. The amino acid residues of the linker peptide should exhibit properties that do not interfere significantly with the activity of the FSH mutant.

The nucleotide sequence encoding the alpha or beta subunits of the FSH mutants of the invention may be constructed by isolating or synthesizing a nucleotide sequence encoding the parent FSH subunit, such as the hFSH-alpha or hFSH-beta with the amino acid sequences shown in FIGS. 6 and 7, respectively or SEQ ID Nos 1 and 2, respectively. The nucleotide sequence is then changed so as to effect the substitution of the relevant amino acid residues. The nucleotide sequence can be modified by site directed mutagenesis as in Example 1 of the present specification. In the alternative, the nucleotide sequence may be prepared by chemical synthesis, wherein oligonucleotides are designed based on the specific amino acid sequence of the FSH mutant.

The nucleotide sequence encoding the polypeptide is inserted into a recombinant vector and operably linked to control sequences necessary for expression of the polypeptide in the desired transfected host cell. One of skill in the art may make a selection among these vectors, expression control sequences and hosts without undue experimentation.

The recombinant vector may be an autonomously replicating vector, i.e. a vector which exists as an extrachromosomal entity, the replication of which is independent of chromosomal replication, e.g. a plasmid. Alternatively, the vector is one which, when introduced into a host cell, is integrated into the host cell genome and replicated together with the chromosome(s) into which it has been integrated.

The vector is preferably an expression vector in which the nucleotide sequence encoding the polypeptide of the invention is operably linked to additional segments required for transcription of the nucleotide sequence. The vector is typically derived from plasmid or viral DNA. A number of suitable expression vectors for expression in the host cells mentioned herein are commercially available or described in the literature.

The recombinant vector may further comprise a DNA sequence enabling the vector to replicate in the host cell in question. An example of such a sequence, (when the host cell is a mammalian cell) is the SV40 origin of replication.

The vector may also comprise a selectable marker, e.g. a gene whose product complements a defect in the host cell, such as the gene coding for dihydrofolate reductase (DHFR) or one which confers resistance to a drug, e.g. ampicillin, kanamycin, tetracycline chloramphenicol, neomycin, hygromycin or methotrexate.

The vector may also comprise an amplifiable gene, such as DHFR, such that cells having multiple copies of the amplifiable gene and flanking sequences, including the mutant FSH DNA, can be selected for on appropriate media.

The term "control sequences" is defined herein to include all components which are necessary or advantageous for the expression of the polypeptide of the invention. Examples of suitable control sequences for directing transcription in mammalian cells include the early and late promoters of SV40 and adenovirus, e.g. the adenovirus 2 major late promoter, the MT-1 (metallothionein gene) promoter and the human cytomegalovirus immediate-early gene promoter (CMV).

The nucleotide sequences of the invention encoding the FSH mutants, whether prepared by site-directed mutagenesis, synthesis, PCR or other methods, may optionally also include a nucleotide sequence that encodes a signal peptide. The signal peptide is present when the polypeptide is to be secreted from the cells in which it is expressed. Such signal peptide, if present, should be one recognized by the cell chosen for expression of the polypeptide. The signal peptide may be homologous (e.g. be that normally associated with a hFSH subunit) or heterologous (i.e. originating from another source than hFSH) to the polypeptide or may be homologous or heterologous to the host cell, i.e. be a signal peptide normally expressed from the host cell or one which is not normally expressed from the host cell.

Any suitable host may be used to produce the polypeptide subunits of the invention, including bacteria, fungi (including yeasts), plant, insect, mammal, or other appropriate animal cells or cell lines, as well as transgenic animals or plants. Examples of suitable mammalian host cells include Chinese hamster ovary (CHO) cell lines, (e.g. CHO-KL; ATCC CCL-61), Green Monkey cell lines (COS) (e.g. COS 1 (ATCC CRL-1650), COS 7 (ATCC CRL-1651)); mouse cells (e.g. NSIO), Baby Hamster Kidney (BI-EK) cell lines (e.g. ATCC CRL-1632 or ATCC CCL-10), and human cells (e.g. BEK 293 (ATCC CRL-1573)), as well as plant cells in tissue culture. Additional suitable cell lines are known in the art and available from public depositories such as the American Type Culture Collection, USA. Methods for introducing exogeneous DNA into mammalian host cells include calcium phosphate-mediated transfection, electroporation, DEAE-dextran mediated transfection, liposome-mediated transfection and viral vectors.

Cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermenters performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g. in catalogues of the American Type Culture Collection). If the polypeptide is secreted into the nutrient medium, it can be recovered directly from the medium. If the polypeptide is not secreted, it can be recovered from cell lysates.

The resulting mutant FSH polypeptide may be recovered by methods known in the art. For example, it may be recovered from the nutrient medium by conventional procedures including, but not limited to, centrifugation, filtration, extraction, spray drying, evaporation, or precipitation.

The mutant FSH polypeptides may be purified by a variety of procedures known in the art including, but not limited to, chromatography (e.g. ion exchange, affinity, hydrophobic, chromatofocusing, and size exclusion), electrophoretic procedures (e.g. preparative isoelectric focusing), differential solubility (e.g. ammonium sulfate precipitation), SDS-PAGE, or extraction.

Use of FSH Mutants:

In one aspect, the invention provides a pharmaceutical composition comprising FSH mutants according to the invention. Such pharmaceutical compositions can be used to stimulate folliculogenesis, for example in conjunction with ovulation induction or assisted reproductive techniques (ART). Because the FSH mutants of the invention is particularly effective in inducing multiple follicles to develop and mature, it is particularly suitable for use in ART, in which it is desired to collect multiple oocytes.

Alternatively, with careful tailoring of the dose, FSH mutants of the invention may be used to induce monofolliculogenesis for OI, or paucifolliculogenesis (up to about three follicles) for IUI, for in vivo fertilisation. Monofolliculogenesis can also be attained with a reduced dose of an FSH mutant, or less frequent dosing as compared with conventional FSH preparations. For example, in OI an FSH preparation of the invention may be administered at 225-400 IU every three days, or lower doses, depending on the patient response. Patient response may be followed by sonography.

The FSH mutants of the invention may be used in a controlled ovarian hyperstimulation (COH) regimen. Standard regimens for COH include a down-regulation phase in which endogenous luteinising hormone (LH) is down-regulated by administration of a gonadotrophin releasing hormone (GnRH) agonist followed by a stimulatory phase in which follicular development (folliculogenesis) is induced by daily administration of follicle stimulating hormone (FSH), usually at about 150-225 IU/day. Alternatively stimulation is started with FSH after spontaneous or induced menstruation, followed by administration of a GnRH-antagonist (typically starting around day six of the stimulatory phase). When there are at least 3 follicles>16 mm (one of 18 mm), a single bolus of hCG (5-10,000 IU) is given to mimic the natural LH surge and induce ovulation. Oocyte recovery is timed for 36-38 hours after the hCG injection.

The FSH mutants of the invention may also be used for OI and IUI. For example, FSH stimulation with a preparation of the invention is started after spontaneous or induced menstruation, at a daily dose of 75-150 IU. When 1 or 3 follicles have reached a diameter of at least 16 mm, a single bolus of hCG is administered to induce ovulation. Insemination is performed in vivo, by regular intercourse or IUI.

Because the FSH mutants of the invention has an increased half-life with respect to known FSH preparations, regimens such as that described above may employ lower IU doses of FSH, and/or may be modified by decreasing the FSH stimulation period, while achieving the same or better response, in terms of number and viability of follicles. For example, using an FSH preparation of the invention, adequate folliculogenesis may be achieved with daily doses of at or about 50-150 IU FSH, preferably at or about 50-100, more preferably at or about 50-75 IU FSH. Dosing of FSH is usually on a daily or semi-daily basis. The dosing period may be less than at or about 14 days, preferably less than at or about 12 days, more preferable less than at or about 11 or 10 days.

For OI, the FSH mutant preparations of the invention may be administered at doses from 25-150 IU FSH/day, preferably, 50-125 IU FSH/day.

For the treatment of male infertility, an FSH mutant preparation of the invention may be administered at 3×150 to 300 IU/week until spermatogenesis reaches levels adequate for insemination, either through regular intercourse or ART techniques.

Because of the longer half-life of the mutant FSH of the invention, it may be administered as a long-acting preparation. Conventional FSH may be administered at or about 300 IU on every second day, while achieving similar results to administration every day at or about 150 IU. The expression "long-acting" is meant to encompass FSH preparations that may be administered less frequently than every two days. Preferred mutant FSH of the invention may be administered every three days, every four days, every five days, every six days or every seven days, while achieving similar or better results than daily administration of conventional FSH.

Pharmaceutical Compositions of the Invention:

In one aspect the FSH mutants or their pharmaceutical compositions according are used for the manufacture of a medicament for treatment of diseases, disorders or conditions.

In another aspect the polypeptide or the pharmaceutical composition according to the invention is used in a method of treating a mammal, in particular a human, comprising administering to the mammal in need thereof such polypeptide or pharmaceutical composition.

It will be apparent to those of skill in the art that an effective amount of a conjugate, preparation or composition of the invention depends, inter alia, upon the disease, the dose, the administration schedule, whether the polypeptide or conjugate or composition is administered alone or in conjunction with other therapeutic agents, the serum half-life of the compositions, and the general health of the patient. Typically, an effective dose of the preparation or composition of the invention is sufficient to ensure a therapeutic effect.

The FSH mutants of the present invention are normally administered in a composition including one or more pharmaceutically acceptable carriers or excipients. "Pharmaceutically acceptable" means a carrier or excipient that does not cause any untoward effects in patients to whom it is administered. Such pharmaceutically acceptable carriers and excipients are well known in the art, and the polypeptide or conjugate of the invention can be formulated into pharmaceutical compositions by well-known methods (see e.g. Remington's Pharmaceutical Sciences, 18th edition, A. R. Gennaro, Ed., Mack Publishing Company (1990); Pharmaceutical Formulation Development of Peptides and Proteins, S. Frokjaer and L. Hovgaard, Eds., Taylor & Francis (2000); and Handbook of Pharmaceutical Excipients, 3rd edition, A. Kibbe, Ed., Pharmaceutical Press (2000)). Pharmaceutically acceptable excipients that may be used in compositions comprising the polypeptide or conjugate of the invention include, for example, buffering agents, stabilizing agents, preservatives, isotonifiers, nonionic surfactants or detergents ("wetting agents"), antioxidants, bulking agents or fillers, chelating agents and cosolvents.

The pharmaceutical composition of the FSH mutants of the invention may be formulated in a variety of forms, including liquids, e.g. ready-to-use solutions or suspensions, gels, lyophilized, or any other suitable form, e.g. powder or crystals suitable for preparing a solution. The preferred form will depend upon the particular indication being treated and will be apparent to one of skill in the art.

The pharmaceutical composition containing a FSH mutant of the invention may be administered intravenously, intramuscularly, intraperitoneally, intradermally, subcutaneously, sublingualy, buccally, intranasally, transdermally, by inhalation, or in any other acceptable manner, e.g. using PowderJect or ProLease technology or a pen injection system. The preferred mode of administration will depend upon the particular indication being treated and will be apparent to one of skill in the art. In particular, it is advantageous that the composition be administered subcutaneously, since this allows the patient to conduct self-administration.

The pharmaceutical compositions of the invention may be administered in conjunction with other therapeutic agents. These agents may be incorporated as part of the same pharmaceutical composition or may be administered separately from the polypeptide or conjugate of the invention, either concurrently or in accordance with any other acceptable treatment schedule. In addition, the polypeptide, conjugate or pharmaceutical composition of the invention may be used as an adjunct to other therapies.

The invention will be illustrated with the following, non-limiting examples.

EXAMPLE 1

Generation of N-linked Glycosylation Mutants of FSH

The cDNAs of the alpha and beta subunits of FSH were subcloned into the pDONR vector (Invitrogen). The QuikChange™ Site-Directed Mutagenesis Kit (Stratagene) was used to introduce the N-linked glycosylation sites into the alpha and beta subunits of FSH. The QuikChange™ system utilizes two synthetic oligonucleotide primers containing the desired mutation(s). The following pairs of oligonucleotides were used to introduce the N-linked glycosylation sites: CC TTG TAT ACA TAC CCA AAC GCC ACC CAG TGT CAC (SEQ ID NO:9) and GTG ACA CTG GGT GGC GTT TGG GTA TGT ATA CAA GG (SEQ ID NO:10) for V78N, GC TGT GCT CAC CAT AAC GAT TCC TTG TAT ACA TAC C (SEQ ID NO:11) and GGT ATG TAT ACA AGG AAT CGT TAT GGT GAG CAC AGC (SEQ ID NO:12) for A70N, GAT CTG GTG TAT AAG AAC CCA ACT AGG CCC AAA ATC CA (SEQ ID NO:13) and TGG ATT TTG GGC CTA GTT GGG TTC TTA TAC ACC AGA TC (SEQ ID NO:14) for D41N/A43T, TGT ACT GTG CGA GGC CTG AAC CCC AGC TAC TGC TCC (SEQ ID NO:15) and GGA GCA GTA GCT GGG GTT CAG GCC TCG CAC AGT ACA (SEQ ID NO:16) for G100N, G AAC GTC ACC TCA AAC TCC ACT TGC TG (SEQ ID NO:17) and CA GCA AGT GGA GTT TGA GGT GAC GTT C (SEQ ID NO:18) for E56N, and CAG GAA AAC CCA ACC TTC TCC CAG CC (SEQ ID NO:19) and GG CTG GGA GAA GGT TGG GTT TTC CTG (SEQ ID NO:20) for F17T. The sequence of the mutants was confirmed by using the ABI PRISM BigDye™ Terminator v3.0 Ready Reaction Cycle Sequencing Kit followed by analysis with the ABI PRISM 310 Genetic Analyzer.

EXAMPLE 2

In vitro Activity of N-Linked Glycosylation Mutants

The pCI mammalian expression vector (Promega) was converted into a GATEWAY destination vector by using the GATEWAY Vector Conversion System (Invitrogen). The alpha and beta mutants along with the conventional recombinant subunits were subcloned into the pCI expression vector using the Gateway™ Cloning Technology (Invitrogen). The pCI expression vector contains the human cytomegalovirus immediate-early enhancer/promoter to regulate the expression of the inserted gene, an intron upstream of the gene to promote expression and the simian virus 40 late polyadenylation signal downstream from the inserted gene to terminate transcription. The E56N and F17T alpha mutants in pCI were co-transfected with conventional recombinant FSH beta in pCI whereas the A70N, G100N, V78N and D41N/A43T beta mutants in pCI were co-transfected with conventional recombinant alpha subunit in pCI. As a control, the conventional recombinant beta subunit of FSH in pCI and the alpha subunit in pCI were co-transfected. The plasmids were transiently transfected into HEK293 cells (ATTC, CRL-10852) using the calcium phosphate method (Wurm patent). One day after the transfection the medium was changed to DMEM/F12 (Invitrogen, 11320-033) containing 1 ug/ml of insulin (Invitrogen, 18140-020), 6.8 ng/ml of sodium selenite (Sigma, S5261) and 12.2 ng/ml of ferric citrate (Sigma, F3388). One day following the change in the medium, the conditioned medium was collected and centrifuged for 5 min at approximately 800×g at 4° C. to remove any cellular debris. The concentration of the FSH in the conditioned medium was determined with an ELISA Kit specific for FSH (Alpha Diagnostic International, 0200).

The agonist activity of the FSH mutants and conventional recombinant FSH was tested in a CHO/FSHR/Luc assay. In this assay a Chinese Hamster Ovary (CHO) cell line was stably transfected with the human FSH receptor and a luciferase reporter gene under the regulation of the cAMP response element (CRE). An agonist of the FSH receptor increases the level of cAMP in the cell that results in the activation of the CREB (cAMP response element binding) protein. This protein interacts with the CRE on the DNA and results in increased transcription of the luciferase gene which is downstream of this element. Varying amounts of conditioned medium from the transient transfections were added to the CHO/FSHR/Luc cells and after a 3.5 hour incubation the amount of the luciferase in the treated cells was measured with the LucLite Luciferase Reporter Gene Assay Kit (Packard BioScience, 6016911) and a TopCount NXT Microplate Scintillation and Luminescence Counter (Packard). All six N-linked glycosylation mutants had activity in the CHO/FSHR/Luc assay comparable to conventional recombinant FSH (See FIGS. 1, 2, 3, and 4).

EXAMPLE 3

Analysis of an N-Linked Glycosylation Mutant

The pCI plasmid containing either the conventional recombinant beta subunit or the V78N beta mutant was co-transfected with conventional recombinant alpha subunit in pCI. The plasmids were transiently transfected into CHO cells using the Lipofectamine 2000 method (Invitrogen, ). The day after the transfection, cells were labeled with

[35S]cysteine by incubating the cells in DMEM-methionine, cystine and L-glutamine (Sigma, D0422) containing 4 mM of L-glutamine, 15 ug/ml of L-methionine, 1% dialyzed fetal bovine serum (Invitrogen, 26400-044) and 100 uCi/ml of [35S]cysteine (Amersham-Pharmacia, SJ15232) for four hours. The conditioned medium was removed and centrifuged at 16,000×g in a Biofuge fresco (Heraeus Instruments) for 5 minutes and then the medium was further clarified by filtering through a 0.45 um Acrodisc filter (Gelman Sciences, 4184). To the clarified medium, 1 M tris, pH 7.4 was added for a final concentration of 50 mM and Tween20 was added for a final concentration of 0.1%. Sepahrose C1-4B coupled to a monoclonal antibody directed against the beta subunit of FSH was added to immunoprecipitate the labeled FSH. The immunoprecipitate was washed three times with a solution containing 50 mM tris, pH 7.4, 0.1% Tween 20 and 150 mM sodium chloride followed by a one wash with 50 mM tris, pH 7.4. Tris-glycine Sample buffer containing dithiothreitol (Jule, Inc., TGSB2XR) was added to the immunoprecipitate and heated to approximately 100° C. for three minutes and centrifuged at 16,000×g in a Biofuge fresco (Heraeus Instruments) for 5 minutes. The supernatant was loaded onto a pre-cast 12% polyacrylamide Tris-glycine gel (Jule Inc., HLC156) and the gel was run at 125 V for 12 hours in a Hoefer SE400 electrophoresis unit. Following the electrophoresis the gel was placed in a fixing solution containing 40% methanol and 10% acetic acid for 30 minutes at room temperature and then in a glycerol solution containing 10% acetic acid and 1% glycerol for 30 minutes. The gel was dried on a Bio-Rad model 583 gel-dryer at 80° C. for 1 hour. After drying, the gel was exposed to a Molecular Dynamics Phosphorimager: 455SI for 20 hours. The results show that the beta subunit of V78N mutant has a larger molecular mass than the beta subunit of conventional recombinant FSH, indicating that the V78N mutant is glycoylated at the introduced site.

EXAMPLE 4

Prep Scale Generation of Mutant FSH

The cDNAs of the alpha- and beta-subunits of human FSH were subcloned into the pDONR vector (Invitrogen). The QuikChange™ Site-Directed Mutagenesis Kit (Stratagene) was used to introduce N-linked glycosylation sites into the alpha- and beta-subunits of FSH. The QuikChange™ system utilises two synthetic oligonucleotide primers containing the desired mutation(s). The following pairs of oligonucleotides were used to introduce the N-linked glycosylation sites: CC TTG TAT ACA TAC CCA AAC GCC ACC CAG TGT CAC (SEQ ID NO:9) and GTG ACA CTG GGT GGC GTT TGG GTA TGT ATA CAA GG (SEQ ID NO:10) for V78N, GC TGT GCT CAC CAT AAC GAT TCC TTG TAT ACA TAC C (SEQ ID NO:11) and GGT ATG TAT ACA AGG AAT CGT TAT GGT GAG CAC AGC (SEQ ID NO:12) for A70N, GAT CTG GTG TAT AAG AAC CCA ACT AGG CCC AAA ATC CA (SEQ ID NO:13) and TGG ATT TTG GGC CTA GTT GGG TTC TTA TAC ACC AGA TC (SEQ ID NO:14) for D41N/A43T, TGT ACT GTG CGA GGC CTG AAC CCC AGC TAC TGC TCC (SEQ ID NO:15) and GGA GCA GTA GCT GGG GTT CAG GCC TCG CAC AGT ACA (SEQ ID NO:16) for G100N, G AAC GTC ACC TCA AAC TCC ACT TGC TG (SEQ ID NO:17) and CA GCA AGT GGA GTT TGA GGT GAC GTT C (SEQ ID NO:18) for E56N, and CAG GAA AAC CCA ACC TTC TCC CAG CC (SEQ ID NO:19) and GG CTG GGA GAA GGT TGG GTT TTC CTG (SEQ ID NO:20) for F17T. The DNA sequences of the mutant cDNAs were confirmed using the ABI PRISM BigDye™ Terminator v3.0 Ready Reaction Cycle Sequencing Kit followed by analysis with the ABI PRISM 310 Genetic Analyzer.

The pCI mammalian expression vector (Promega) was converted into a GATEWAY destination vector by using the GATEWAY Vector Conversion System (Invitrogen). The alpha- and beta-mutants along with the wild-type subunits were subcloned into the pCI expression vector using the Gateway™ Cloning Technology (Invitrogen). The pCI expression vector contains the human cytomegalovirus immediate-early enhancer/promoter to regulate the expression of the inserted gene, an intron upstream of the gene to promote expression and the simian virus 40 late polyadenylation signal downstream from the inserted gene to terminate transcription. The E56N and F17T alpha mutants in pCI were co-transfected with wild-type FSH beta in pCI whereas the A70N, G100N, V78N and D41N/A43T beta-mutants in pCI were co-transfected with wild-type alpha-subunit in pCI. As a control, the wild-type beta-subunit of FSH in pCI and the alpha-subunit in pCI were co-transfected. The plasmids were transiently transfected into HEK293 cells (ATTC, CRL-10852) using the calcium phosphate method (for example, as described in WO 96/07750). Alternatively, The pCI plasmid containing either the wild-type beta-subunit or the V78N beta-mutant was co-transfected with wild-type alpha-subunit in pCI. The plasmids may also be transiently or stably transfected into CHO cells. One day after the transfection the medium was changed to DMEM/F12 (Invitrogen, 11320-033) containing 1 ug/mil of insulin (Invitrogen, 18140-020), 6.8 ng/ml of sodium selenite (Sigma, S5261) and 12.2 ng/ml of ferric citrate (Sigma, F3388). One day following the change in the medium, the conditioned medium was collected and centrifuged for 5 min at approximately 800×g at 4° C. to remove any cellular debris. The supernatant was removed and centrifuged at 16,000×g in a Biofuge fresco (Heraeus Instruments) for 5 minutes and then the medium was further clarified by filtering through a 0.45 μm Acrodisc filter (Gelman Sciences, 4184). To the clarified cellular extract was added, 1 M Tris, pH 7.4 for a final concentration of 50 mM Tris and Tween20 was added for a final concentration of 0.1% Tween20.

The FSH mutants were purified from the cellular extract using immuno-affinity chromatography, on Sepharose derivatised with anti-FSH monoclonal antibodies immobilised using divinyl sulfone (Immunoresin anti-FSH-McAb-DVS-Sepharose). Such resins can be produced by methods known to the skilled practitioner, for example, as disclosed in WO 88/10270.

The resin was equilibrated in equilibrating buffer, consisting of 0.1M Tris-HCl, 0.3M NaCl buffer at pH=7.5, at 4° C. The column was loaded with a quantity of IU FSH (by radio-immunoassay, RIA) corresponding to 80-90% of the total FSH binding capacity of the column.

Non-retained proteins were eluted with equilibrating buffer (as above) until the $OD_{280}$ of the eluate was lower than 0.02.

The absorbed mutant FSH was eluted from the immunoresin with 1M ammonia solution at 4° C. Eluates corresponding to about 4 times the immunoresin volume were pooled, the pH was adjusted to 9.0 by addition of glacial acetic acid at 4° C., as soon as possible after collection, and the solution was ultrafiltered in an Amicon apparatus (membrane cutoff 10,000 Da) and concentrated to a small volume.

The concentrated mutant FSH solution was then subjected to a step of reverse phase HPLC, using a Waters Prep LC 500A liquid chromotograph equipped with UV detector and a preparative gradient generator. Prior to application to the column, the pH of the solution was adjusted to about 5.6. The solution was loaded on a $C_{18}$ reversed phase column (Prepak 500 $C_{18}$ cartridges Waters) which had previously been equilibrated with 0.05 M ammonium acetate buffer pH=5.6 at room temperature. The flow rate was 100 ml/min and the eluate was monitored at 280 nm.

Mutant FSH was eluted by a gradient of isopropanol up to 50% of the mobile phase. Fractions were checked by analytical gas phase chromatography (GPC). and radioimmunoassay (RIA). The organic solvent was removed by distillation under vacuum at less than 40° C., and the solution was frozen and lyophilized.

All publications and patent applications cited in this specification are herein incorporated by reference as if each individual publication or patent application were specifically and individually indicated to be incorporated by reference. Although the foregoing invention has been described in some detail by way of illustration and an example for purposes of clarity of understanding, it will be readily apparent to those of ordinary skill in the art in light of the teachings of this invention that certain changes and modifications may be made thereto without departing from the spirit or scope of the appended claims.

REFERENCES

1) Fox K M, Dias J A, Van Roey P, 2001. Three-dimensional structure of human follicle-stimulating hormone. Mol Endocrinol., 15:378.
2) Wu H. et al, 1994. Structure of human chorionic gonadotropin at 2.6 A resolution from MAD analysis of the selenomethionyl protein. Structure. 2:545.
3) Tegoni M et al, 1999. Crystal structure of a ternary complex between human chorionic gonadotropin (hCG) and two Fv fragments specific for the alpha and beta-subunits.
4) Jiang X. et al, 1995. Structure predictions for the ligand-binding region of glycoprotein hormone receptors and the nature of hormone-receptor interactions. Structure. 3:1341.

We claim:

1. An isolated mutant of human Follicle Stimulating Hormone (FSH) having FSH activity, wherein one N-glycosylation site has been introduced into the FSH alpha subunit by the mutation F17T.

2. An isolated mutant of human Follicle Stimulating Hormone (FSH) having FSH activity, wherein one N-glycosylation site has been introduced into the FSH alpha subunit by the mutation E56N.

3. An isolated mutant of human Follicle Stimulating Hormone (FSH) having FSH activity, wherein one N-glycosylation site has been introduced into the FSH beta subunit by the mutation A70N.

4. An isolated mutant of human Follicle Stimulating Hormone (FSH) having FSH activity, wherein one N-glycosylation site has been introduced into the FSH beta subunit by the mutation V78N.

5. An isolated mutant of human Follicle Stimulating Hormone (FSH) having FSH activity, wherein one N-glycosylation site has been introduced into the FSH beta subunit by the mutation G100N.

6. An isolated mutant of human Follicle Stimulating Hormone (FSH) mutant having FSH activity, wherein one N-glycosylation site has been introduced into the FSH beta subunit by the mutations D41N/A43T.

7. A composition comprising the FSH mutant according to any one of claims 1-6 and at least one pharmaceutically acceptable carrier or excipient.

8. A method of treating an infertile human, comprising administering to the human in need thereof an effective amount of the human FSH mutant according to any one of claims 1-6.

9. A method of stimulating folliculogenesis in a human, comprising administering to the human an effective amount of the FSH mutant according to any one of claims 1-6.

10. A method of inducing ovarian hyperstimulation in a human, comprising administering to the human an effective amount of the FSH mutant according to any one of claims 1-6.

11. An isolated nucleic acid encoding the FSH mutant of claim 1.

12. An isolated nucleic acid encoding the FSH mutant of claim 2.

13. An isolated nucleic acid encoding the FSH mutant of claim 3.

14. An isolated nucleic acid encoding the FSH mutant of claim 4.

15. An isolated nucleic acid encoding the FSH mutant of claim 5.

16. An isolated nucleic acid encoding the FSH mutant of claim 6.

17. An expression vector comprising the nucleic acid according to any one of claims 11-16.

18. An isolated host cell transformed with a vector according to claim 17.

19. The isolated host cell of claim 18 which is eukaryotic.

20. The isolated host cell of claim 19 which is mammalian.

21. A method for producing a FSH mutant, comprising subjecting the isolated host cell according to claim 18 to cultivation under conditions conducive for expression of the FSH mutant to thereby produce the FSH mutant.

22. A method for producing a FSH mutant, comprising subjecting the isolated host cell according to claim 19 to cultivation under conditions conducive for expression of the FSH mutant to thereby produce the FSH mutant.

23. A method for producing a FSH mutant, comprising subjecting the isolated host cell according to claim 20 to cultivation under conditions conducive for expression of the FSH mutant to thereby produce the FSH mutant.

* * * * *